United States Patent
Platt et al.

(10) Patent No.: US 7,058,442 B1
(45) Date of Patent: Jun. 6, 2006

(54) CYCLING EVENT AND AUTO-TRIGGER MEMORY HANDLING

(76) Inventors: Harry Louis Platt, 14/166 Belmore Road, Randwick, NSW, 2031 (AU); Vladimir Jankov, 14/166 Belmore Road, Randwick, NSW, 2031 (AU)

(*) Notice: Subject to any disclaimer, the term of this patent is extended or adjusted under 35 U.S.C. 154(b) by 533 days.

(21) Appl. No.: 10/009,907

(22) PCT Filed: Jun. 9, 2000

(86) PCT No.: PCT/AU00/00656

§ 371 (c)(1),
(2), (4) Date: Sep. 19, 2002

(87) PCT Pub. No.: WO00/76395

PCT Pub. Date: Dec. 21, 2000

(30) Foreign Application Priority Data

Jun. 10, 1999 (AU) .................................. PQ0885

(51) Int. Cl.
*A61B 5/04* (2006.01)

(52) U.S. Cl. .................................................. 600/509

(58) Field of Classification Search ................ 600/509, 600/522, 523
See application file for complete search history.

(56) References Cited

U.S. PATENT DOCUMENTS 5,732,708 A * 3/1998 Nau et al. .................... 600/523
6,496,715 B1 * 12/2002 Lee et al. .................... 600/424

* cited by examiner

*Primary Examiner*—Robert E. Pezzuto
*Assistant Examiner*—Frances P. Oropeza
(74) *Attorney, Agent, or Firm*—Edwin D. Schindler

(57) ABSTRACT

A method for recording into a memory of a cardiac event recorder, in which the memory of the cardiac event recorder includes a manual trigger memory and an auto-trigger memory, with the auto-trigger memory being partitioned into a plurality of auto-trigger recording partitions, the method includes the steps of continuously recording signals, in the event of a manual trigger, acquired from the manual trigger or the auto-trigger in the manual trigger memory, and copying the signals acquired from the auto-trigger from the manual trigger memory to a partition of the auto-trigger memory.

3 Claims, 1 Drawing Sheet

CYCLING EVENT AND AUTO-TRIGGER MEMORY HANDLING

BACKGROUND OF THE INVENTION

1. Technical Field of the Invention

Figure 1:
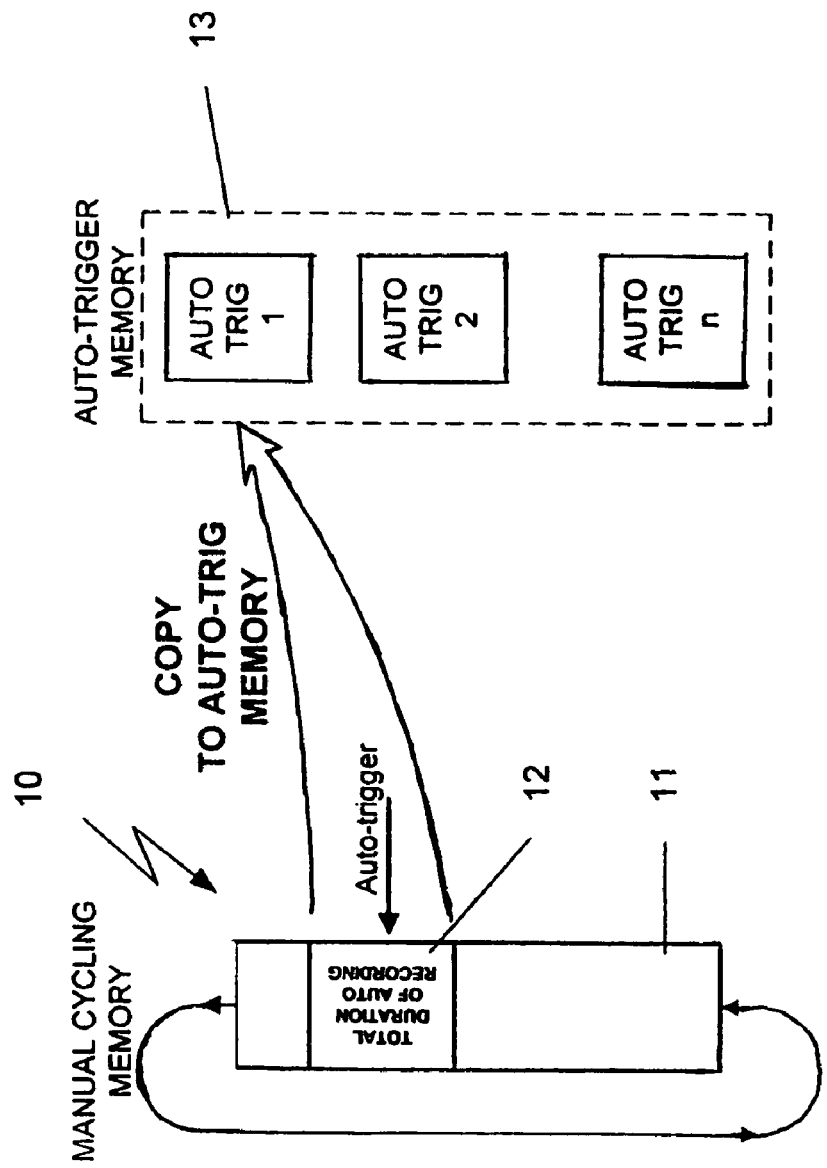

The present invention relates to the field of monitoring a cardiac patient's electri-cal cardiac activity by means of a cardiac event recorder and, in particular, to the memory handling of such cardiac event recorders.

2. Description of the Prior Art

Cardiac event recorders currently known to the prior art generally have only one type of memory used for both manual and auto-triggered ECG recordings. Signal arti-acts and noise can inadvertently cause a false triggering of the auto-trigger with such prior art devices and, thus, fill the memory with useless information.

It would be advantageous to provide a method and apparatus which prevents the memory of cardiac event recorders from being filled with useless information resulting from a false triggering of the auto-trigger.

SUMMARY OF THE INVENTION

It is, therefore, an object of the present invention to provide a method and apparatus for the recording of an ECG which substantially overcomes or ameliorates the above-mentioned disadvantages by preventing memory overflow.

According to one aspect of the present invention, there is disclosed a method of recording into memory of a cardiac event recorder, said method including the steps of subdividing the memory into two parts with the two parts being a manual trigger memory and an auto-trigger memory. Further, partitioning the auto-trigger memory into a plurality of auto-trigger recording partitions, whereby in the event of a manual trigger, acquired signals are recorded continuously in said manual trigger memory and in the event of an auto-trigger, acquired signals are recorded continuously in said manual trigger memory and then copied into one of said plurality of auto-trigger recording partitions Preferably, the recording is done in cycling mode whereby the signal is continu-ously recorded in the manual memory, thus providing a segment of pre-event recording prior to the manual trigger, which records information for a predetermined length of time.

Preferably, if the recording is initiated by the auto-trigger, the cycling mode is not terminated or interrupted.

Preferably, at least two manual trigger recordings are able to be stored in the manual memory.

Preferably, the manual trigger recordings are about 2 to 3 times longer than the auto-trigger recordings.

BRIEF DESCRIPTION OF THE DRAWING FIGURES

The present invention will now be described with reference to the accompanying drawing in which:

FIG. 1 is a diagram showing the memory of the cardiac event recorder.

DETAILED DESCRIPTION OF THE DRAWING FIGURES AND PREFERRED EMBODIMENTS

When recording an ECG using a cardiac event recorder (not illustrated), the data is recorded into RAM 10, which is generally recorded cyclically, i.e., when the memory is full, the data overflows and records over the previously recorded data.

The RAM 10 is subdivided into two parts, i.e., a manual trigger memory 11 and an auto-trigger memory 12. The auto-trigger memory 12 is further partitioned into a number of auto-trigger memory recordings 13.

In this cyclic recording mode, the data is continuously recorded into the manual trigger memory 11 and, thus, when a manual trigger is received, this fact is recorded. The data recorded after a manual trigger is then stored in the manual trigger memory 11 with at least two manual triggered recordings being stored in the manual memory. In this cyclic memory mode, a segment of pre-event recording is also stored in the manual memory 11.

If an auto-trigger function initiated the trigger, the cycling mode is not terminated or interrupted (unlike the manual trigger.) After the duration of the auto-triggered event, which is recorded in the manual memory 11, it is copied into one of the partitions 13 of the auto-trigger memory 12.

The foregoing describes only one embodiment of the present invention, and modi-fications obvious to those skilled in the art can be made thereto without departing from the scope of the present invention.

The invention claimed is:

1. A method for recording into a memory of a cardiac event recorder, said memory being subdivided into a manual trigger memory and an auto-trigger memory with said auto-trigger memory being partitioned into a plurality of auto-trigger recording partitions, said method comprising the steps of:

continuously recording signals acquired from a manual trigger or an auto-trigger in the manual trigger memory; and, copying said signals acquired from the auto-trigger from the manual trigger memory to a recording partition of said plurality of auto-trigger recording partitions of the auto-trigger memory.

2. The method for recording into a memory of a cardiac event recorder according to claim 1, wherein said step of continuously recording signals from said manual trigger or said auto-trigger is carried out in a cycling mode.

3. The method for recording into a memory of a cardiac event recorder according to claim 1, wherein said manual trigger memory stores at least two said signals acquired from said manual trigger.

* * * * *